United States Patent [19]

Urdea et al.

[11] Patent Number: 5,132,204
[45] Date of Patent: Jul. 21, 1992

[54] CHEMILUMINESCENT DOUBLE-TRIGGERED 1,2-DIOXETANES

[75] Inventors: Michael S. Urdea, Alamo; Brian D. Warner, Martinez, both of Calif.

[73] Assignee: Chiron Corporation, Emeryville, Calif.

[21] Appl. No.: 359,485

[22] Filed: May 31, 1989

[51] Int. Cl.⁵ .............. C07D 319/02; C12Q 1/00; C12Q 1/28; C12Q 1/42
[52] U.S. Cl. .............. 435/4; 435/7.72; 435/21; 435/28; 252/700; 558/70; 549/200; 549/218
[58] Field of Search .............. 435/6, 8, 4, 21, 28; 252/700; 536/1.1, 29, 115; 530/802; 538/70; 568/716; 549/218

[56] References Cited

U.S. PATENT DOCUMENTS

| | | | |
|---|---|---|---|
| 3,720,622 | 3/1973 | Bollyky | 252/700 |
| 4,931,223 | 6/1990 | Bronstein | 252/700 |
| 4,959,182 | 9/1990 | Schaap | 252/700 |

FOREIGN PATENT DOCUMENTS 10254051  1/1988  European Pat. Off. .
18800695  1/1988  PCT Int'l Appl. .

OTHER PUBLICATIONS

Schaap et al., (1987), Tetrahedron Letters, vol. 28, No. 11, pp. 1155-1158, 1159-1162.
McCapra, (1968) Chemical Communications, pp. 155-156.
Kopecky et al., (1969) Canadian Journal of Chemistry 47:709-711.
Wieringa et al., (1972) Tetrahedron Letters 2:169-172.

Primary Examiner—Ronald W. Griffin
Assistant Examiner—Gary L. Kunz
Attorney, Agent, or Firm—Morrison & Foerster

[57] ABSTRACT

A stable 1,2-dioxetane of the formula:

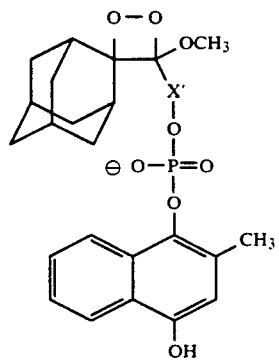

wherein X' is a phenyl group with 0 to 2 Cl or I atoms. This 1,2-dioxetane is a double-trigger substrate. The 2-methyl-4-hydroxy-naphthyl group is first removed by horseradish peroxidase. The exposed phosphate group is then removed with alkaline phosphatase. The exposed phenoxy 1,2-dioxetane decomposes to generate chemiluminescence output in immunoassays or nucleic acid hybridization assays.

2 Claims, 9 Drawing Sheets

CARBOXYPEPTIDASE A

HYDROXYLAMINE

FIG. 4C $R_4 = -(CH_2)_4-NH_2,$
$-(CH_2)_3-NH\overset{\underset{\|}{NH\oplus}}{C}-NH_2;$ CARBOXYPEPTIDASE B

FIG. 4F $R_5$ = $CH_3-$, $(CH_3)_2CH-$, $CH_3CH_2-(CH_3)CHCH_2-$, Ph—$CH_2-$ ; CARBOXYPEPTIDASE A

CHEMILUMINESCENT DOUBLE-TRIGGERED 1,2-DIOXETANES

TECHNICAL FIELD

The present invention relates to 1,2-dioxetanes that can be triggered by sequential treatment with two different activating agents to generate light and the use of such dioxetanes in biochemical assays.

BACKGROUND

The involvement of dioxetane intermediates in chemiluminescent reactions was first postulated in (1968) 155. It was suggested that luciferin under the action of luciferase formed an unstable dioxetane intermediate which decomposed to produce light.

Kopecky and Mumford, Can J. Chem. (1969) 47:709 produced 3,3,4-trimethyl dioxetane which was shown to thermally decompose to acetone and aldehyde with the generation of light. Such alkyl dioxetanes are, however, too unstable at room temperature to render them useful generators of light in chemical assays.

More stable 1,2-dioxetanes were produced by replacing the alkyl groups with polycyclic hydrocarbon groups. Weiringa et al synthesized adamantlyideneadamantane 1,2-dioxetane via photooxygenation of adamantylideneadamantane, Tetrahedron. Lett. (1972) 169. This dioxetane proved to be extremely thermostable—in fact so stable that it would require detection temperatures in excess of 150° C. Such elevated temperatures make the use of this dioxetane in assays of biological samples very difficult.

EPA Publication No. 0 254 051 reports the first chemically triggered 1,2-dioxetanes. See also WO 88/00695. These dioxetanes retain an adamantyl substituent on one carbon atom of the peroxide ring for stability and have an aroxy substituent protected with a group such as a phosphate, silyl, or acetyl group on the other carbon atom of the ring. These dioxetanes are sufficiently stable as long as the protecting group is present. However, once the group is removed, such as by the action of alkaline phosphatase in the case of phosphate protection or fluoride ion in the case of silyl protection, the resulting oxide intermediate is unstable and rapidly decomposes to ketones with efficient light production. While several such triggerable dioxetanes have been reported, those that provide a dioxetane that is a substrate for alkaline phosphatase (AP) have proven to be most useful both in immunoassays and in nucleic acid hybridization assays. Even though use of these AP-triggered dioxetanes has provided more sensitive assays than other nonisotopic assay formats, they still suffer from two problems. One relates to non-specific binding. The limit of detection of these assays is mostly dictated by non-specific binding of assay components leading to AP bound to surfaces independent of the presence of target molecules (noise). AP is a particularly problematic enzyme label with respect to non-specific binding. AP is ubiquitous. Its use as a specific label can be complicated by reagent and sample contamination with low levels of AP from adventitious sources. The other problem relates to the time frame of light generation. Once triggered with AP a slow (15-120 min) rate acceleration is observed followed by a constant steady state turnover (1-6 hr, depending upon the target and thus the enzyme concentration). Accordingly, at low target concentration, accumulation with an integrating detector of the total light output can take many hours. Also, there is the constant reagent-associated background light emission during the entire steady state turnover that limits detection at low non-specific binding. The present invention addresses both of these problems.

DISCLOSURE OF THE INVENTION

The invention resides in the development of novel stable 1,2-dioxetanes which include two protecting groups that are removed sequentially by different processes to produce an unstable oxide intermediate. The removal of the first protecting group is triggered by the label used in the assay. This removal does not, however, destabilize and activate the dioxetane. It merely deprotects the second protecting group. A trigger other than AP which is not ubiquitous and which exhibits low non-specific binding and higher turnover may be used to remove the first protecting group. Further the concentration of target molecule (label) is not involved in the removal of the second protecting group which triggers the dioxetane decomposition and light generation. The concentration of the second trigger or deprotecting agent (e.g., AP) can be adjusted to optimize the time frame of signal generation. Also, reducing the time for the target dependent output to occur may provide an increase in the signal-to-noise ratio and thus the sensitivity of the assay.

Accordingly, one aspect of the invention are novel stable 1,2-dioxetanes of the formula:

where $R_1$, $R_2$, and $R_3$ are passive organic groups that allow the dioxetane to decompose and produce light when Z and Y are removed, with the proviso that $R_1$ and $R_2$ may be joined to form a cyclic moiety, Z is a first protecting group that can be removed by a first deprotecting process, Y is a second protecting group that can be removed by a second deprotecting process, and X is an organic group which upon removal of Z and Y renders the dioxetane susceptible to said decomposition, with the proviso that X may be joined to $R_3$ to form a cyclic moiety.

Another aspect of the invention is a method for generating light comprising:

(a) providing a stable 1,2-dioxetane of the formula:

where $R_1$, $R_2$, and $R_3$ are passive organic groups that allow the dioxetane to decompose and produce light when Z and Y are removed, with the proviso that $R_1$ and $R_2$ may be joined to form a cyclic moiety, Z is a first protecting group that can be removed by a first deprotecting process, Y is a second protecting group that can be removed by a second deprotecting process, and X is an organic group which upon removal of Z and Y renders the dioxetane susceptible to said decomposition, with the proviso that X may be joined to $R_3$ to form a cyclic moiety;

(b) removing the first protecting group Z; and
(c) removing the second protecting group Y.

Still another aspect of the invention is a chemiluminescent method for detecting a component in a sample suspected of containing the component wherein the component is detected via a label carried by a ligand that specifically complexes or binds to the component comprising:
(a) binding a labeled ligand to the component;
(b) contacting the component-labeled liquid complex with a dioxetane of the formula where $R_1$, $R_2$, and $R_3$ are passive organic groups that allow the dioxetane to decompose and produce light when Z and Y are removed, with the proviso that $R_1$ and $R_2$ may be joined to form a cyclic moiety. Z is a first protecting group that can be removed by a first deprotecting process, Y is a second protecting group that can be removed by a second deprotecting process, and X is an organic group which upon removal of Z and Y renders the dioxetane susceptible to said decomposition, with the proviso that X may be joined to $R_3$ to form a cyclic moiety, whereby Z is removed through reaction with the label on the complex;
(c) contacting the partly deprotected dioxetane with an activating agent that removes Y to produce an unstable oxide intermediate which decomposes to form light; and
(d) detecting said light.

Yet another aspect of the invention is a chemiluminescent signal generating reagent kit for use in generating a chemiluminescent signal in an assay for a component of a sample wherein the component is detected via an enzymatic label carried by a ligand that specifically complexes or binds to the component comprising in packaged combination:
(a) a first container containing a dioxetane of the formula where $R_1$, and $R_2$, and $R_3$ are passive organic groups that allow the dioxetane to decompose and produce light when Z and Y are removed, with the proviso that $R_1$ and $R_2$ may be joined to form a cyclic moiety, Z is a first protecting group that can be removed by reaction with said enzymatic label, Y is a protecting group that can be removed by reaction with a deprotecting agent other than said enzymatic label, and X is an organic group which upon removal of Z and Y renders the dioxetane susceptible to said decomposition, with the proviso that X may be joined to $R_3$ to form a cyclic moiety, whereby Z is removed through reaction with the label on the complex; and
(b) a second container containing said deprotecting agent.

BRIEF DESCRIPTION OF THE DRAWINGS

FIG. 4 depicts the chemical structures of examples of 1,2-dioxetanes of the invention.

FIG. 5 is a schematic flow diagram depicting the chemical synthesis used to make the 1,2-dioxetane starting material shown in FIG. 2.

FIG. 6 is a schematic flow diagram depicting the chemical synthesis used to make the 1,2 dioxetane of Example 2.

MODES FOR CARRYING OUT THE INVENTION

As used herein the term "stable" used to describe the 1,2-dioxetanes of the invention intends that the molecule undergoes no significant decomposition at approximately 25° C. in aqueous media that does not contain agents that remove the two protecting groups from the dioxetane.

$R_1$ and $R_2$ in the above formula will normally represent hydrocarbyl groups which either separately or joined together form a sterically bulky group that stabilizes the peroxide ring. Preferably they are joined to form a spirofused carbocyclic group of 6 to 30 carbon atoms. Most preferably, they are joined and represent an adamantane group. Correspondingly, $R_3$ represents a group that provides the dioxetane with water solubility and/or is a fluorescent group such as fluorescein or the like. $R_3$ will normally represent a group containing 1 to 18 carbon atoms selected from alkyl, alkoxy, monocyclic aryloxy, dialkylamino, dimonocyclic arylamino, trialkyl silyloxy, trimonocyclic aryl silyloxy or will be joined to X to form an oxy substituted aryl radical, such as a naphthyl, fluorenyl, or xanthenyl group, of 6 to 30 carbon atoms. Preferably $R_3$ represents an alkoxy group of 1 to 8 carbon atoms with methoxy being particularly preferred. When X is not joined to $R_3$ it will normally represent an oxy-substituted aryl group of 6 to 30 atoms and may be monocyclic such as phenyl, or polycyclic such as naphthyl. Preferably X is a phenoxy group optionally substituted with up to two Cl or I groups.

The protecting groups Y and Z may be selected from labile groups that may be removed with a deprotecting agent such as an enzyme, base, or fluoride ion, with the proviso that both are not removed by the same agent. It is thus intended that the two groups will be removed sequentially beginning with Z by different agents and treatments to leave the XO⁻ group bonded to the peroxide ring which initiates decomposition of the dioxetane. Preferably Z is a protecting group that may be removed by an enzyme. Most preferably the protecting groups are selected so as to each be removed through the action of a different enzyme. In other words, the presence of Z makes the dioxetane a substrate for a first enzyme and the presence of Y makes the dioxetane a substrate for a second enzyme. Of course, Z must be bonded to Y by a cleavable linkage. Examples of enzymatically cleavable groups are phosphate cleavable by alkaline or acid phosphatases, alkyl esters cleavable by esterases, carboxyl cleavable by decarboxylases, beta-D-xyloside cleavable by beta-xylosidase, AMP analogs cleavable by 5' nucleotidase, galactosides cleavable by galactosidases, glucosides cleavable by glucosidases, and mannosides cleavable by mannosidases.

In general, these dioxetanes are synthesized from commercially available materials in the following manner. The hydroxyarylalkoxymethylene adamantane is synthesized as indicated in FIG. 5 (adamantane synthon; compound 8). A separate synthon is prepared containing the X, Y and Z functions (XYZ synthon). Except for the nucleophile (HO—, HOOC—, HO₃.PO—, etc.) on the X function to be condensed with the hydroxyaryl of the adamantane all potential reactive sites are temporarily protected with appropriate blocking groups. The nucleophile can be activated (e.g., N-hydroxysuccinimydyl carboxyl, N,N-diisopropylaminophosphinyl). The XYZ synthon is condensed to the hydroxylaryl function of the adamantane synthon usually in the presence of a condensing agent (e.g., carbodiimide for carboxyl or tetrazole for the phosphinyl as in preparation of compound 9 in FIG. 5). The temporary protecting functions of the XYZ synthon are then selectively removed. Upon purification of the desired condensation product, the alkene function is photooxidized to yield the 1,2-dioxetane. This product can be purified, usually by precipitation from an appropriate solvent.

Figure 1:
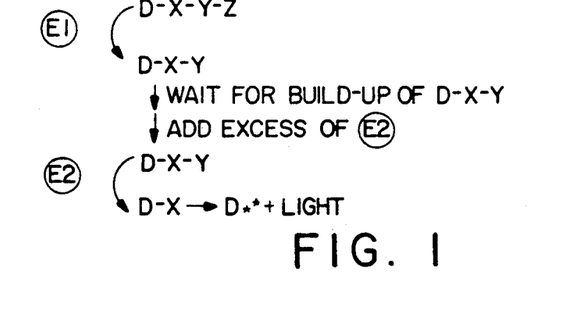
FIG. 1 is a schematic depiction of the process by which the protecting groups are removed from the invention dioxetanes to produce an unstable oxo intermediate that decomposes and produces light.

FIG. 1 illustrates the process by which the dioxetanes of the invention are triggered to decompose and produce light. For convenience the triggers are both enzymes, designated E1 and E2. The symbol D represents the basic dioxetane moiety (the peroxide ring plus $R_1$, $R_2$, and $R_3$). As illustrated, the dioxetane is added to an aqueous medium containing E1. In immunoassays and nucleic acid hybridization assays E1 will be directly or indirectly bound to a substance (e.g. an antigen or antibody in immunoassays or a nucleic acid probe in hybridization assays) that has specific affinity for the target substance being detected. Under the action of E1 Z is cleaved from the dioxetane leaving the moiety D-X-Y. After a sufficient build up of D-X-Y an excess of E2 is added to the medium. D-X-Y is a substrate for E2 and Y is removed from the dioxetane leaving the unstable oxo intermediate D-X which decomposes to ketones with concomitant light output.

Figure 2:
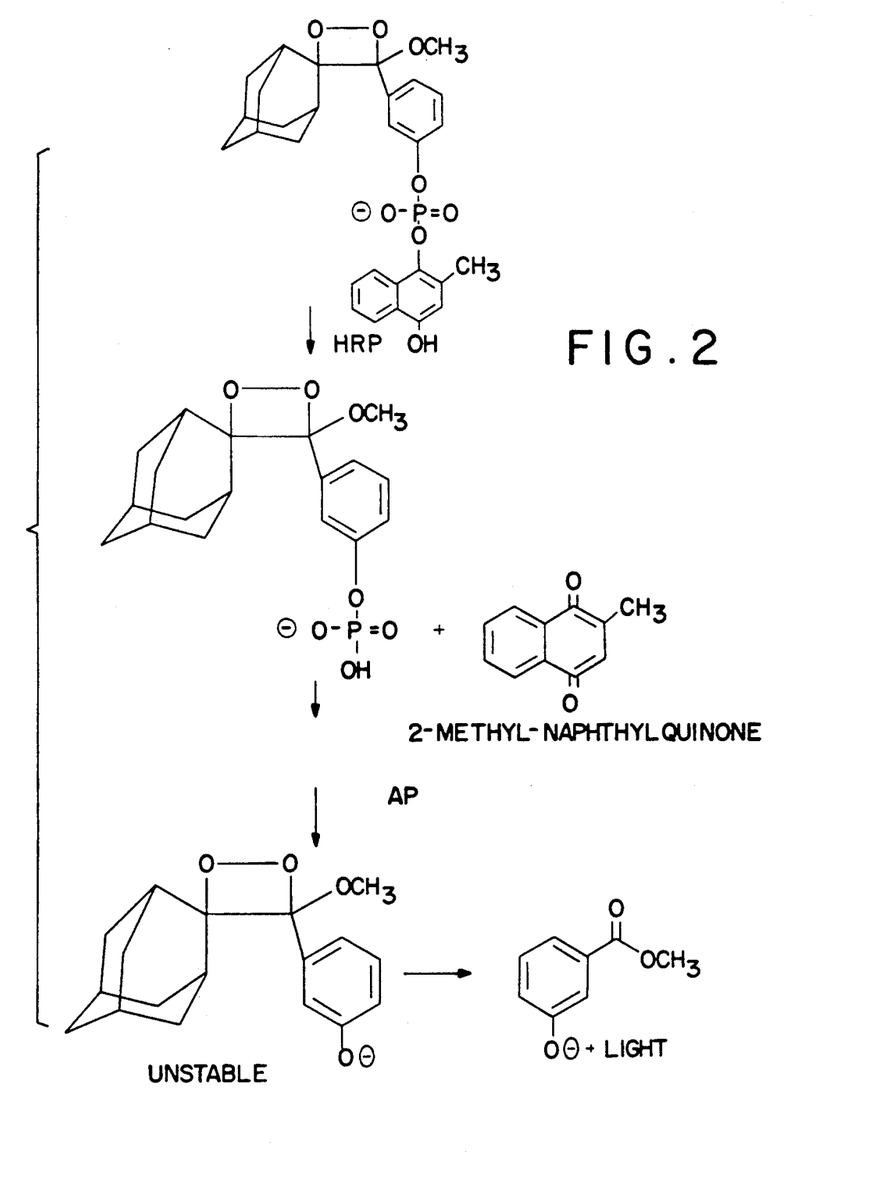
FIG. 2 is a schematic flow diagram of a specific embodiment of the process shown in FIG. 1.

FIG. 2 depicts a specific embodiment of the process shown in FIG. 1. In this instance the dioxetane is 4-[(3-hydroxyl-2-methylnaphthylene-1-phosphoryl)phenyl]-4-methoxy-spiro [1,2-dioxetane-3,2'-adamantane], the first enzyme (E1) is horseradish peroxidase (HRP) that is the label in the assay and the second enzyme (E2) is alkaline phosphatase. The concentration of HRP is proportional to the target concentration whereas the AP concentration is unrelated to target or HRP concentration. In the absence of HRP (target) no signal would be obtained. In the presence of HRP the naphthylene moiety is cleaved from. the dioxetane. After the HRP reaction, an excess of AP is added which removes the phosphate group and activates decomposition of the dioxetane. Through use of relatively large quantities of AP the light output can be generated and recorded in a shorter time frame (seconds to minutes rather than hours) than when a single triggered dioxetane is used where the AP concentration is proportional to the target concentration. It should also be noted that the light output can be regulated at will by adjusting the AP concentration.

Figure 3:
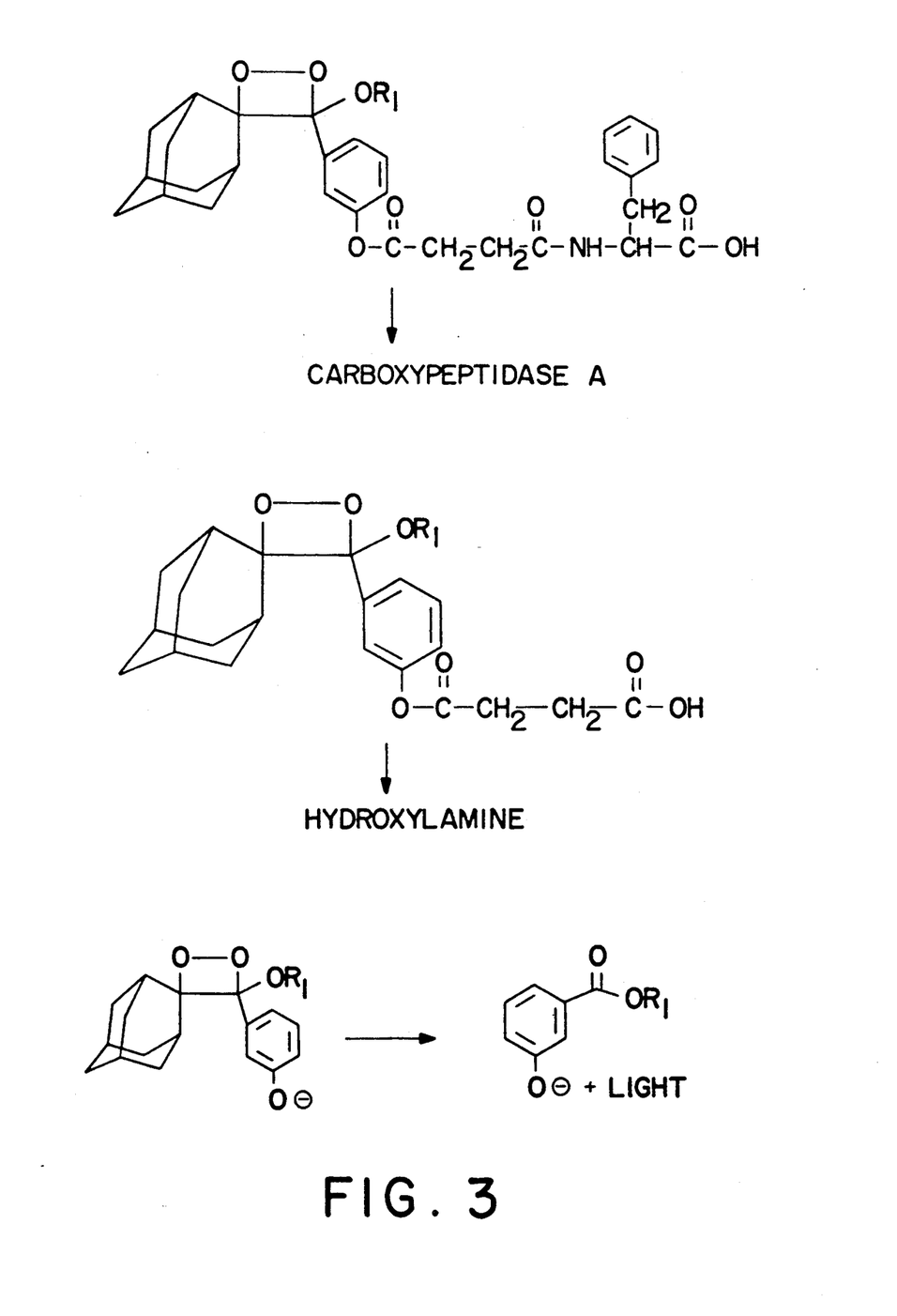
FIG. 3 is a schematic flow diagram of a variation of the process shown in FIG. 1.
Figure 4A:
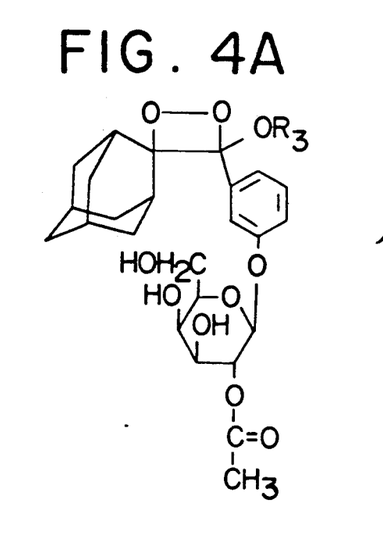
FIG. 4A is as esterase/B-galactosidase double-trigger substrate.
Figure 4B:
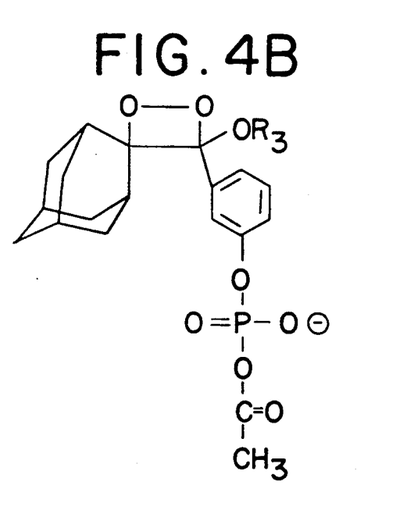
FIG. 4B is an esterase/phosphatase double-trigger substrate.
Figure 4C:
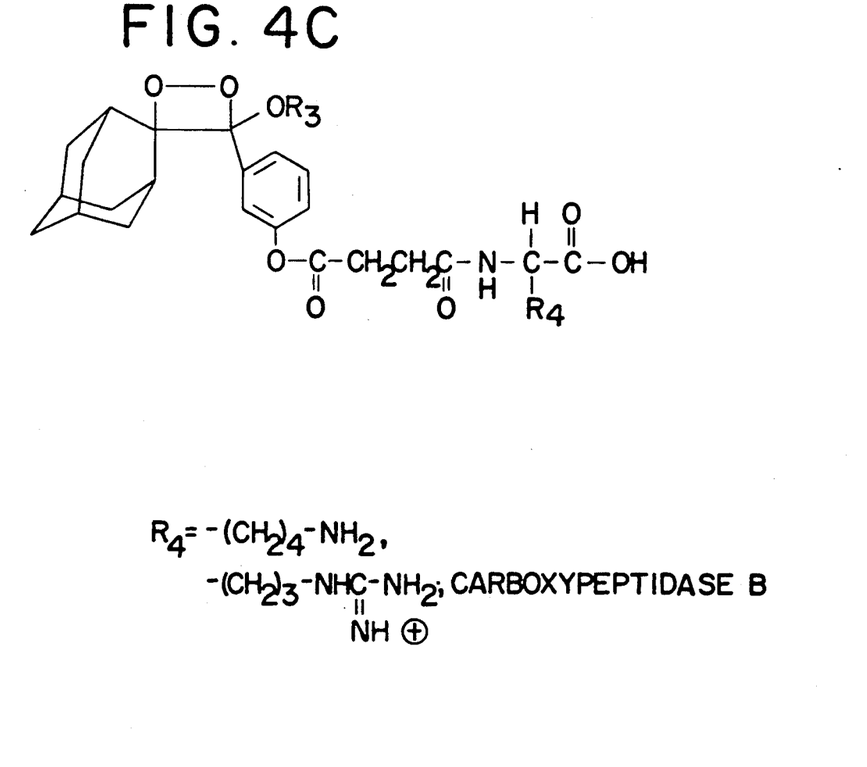
FIG. 4C is a carboxypeptidate/hydroxylamine double-trigger substrate.
Figure 4D:
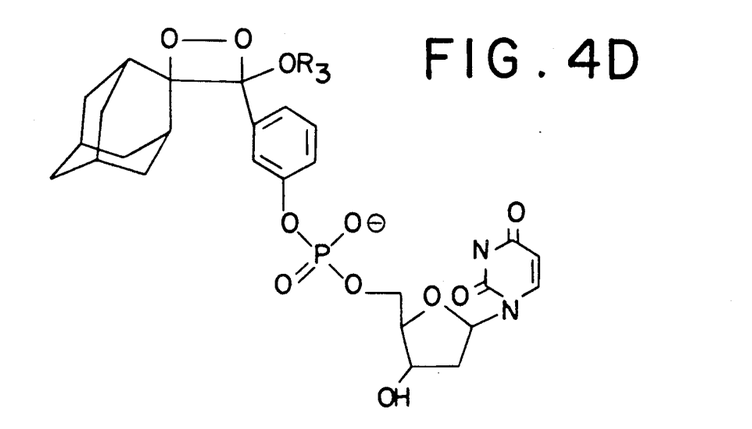
FIG. 4D is a 5'-nucleotidase/phosphatase double-trigger substrate.
Figure 4E:
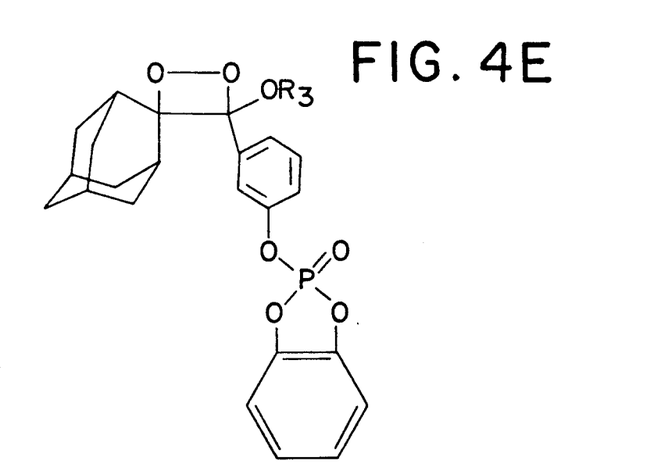
FIG. 4E is a horseradish peroxidase/phosphatase double-trigger substrate.
Figure 4F:
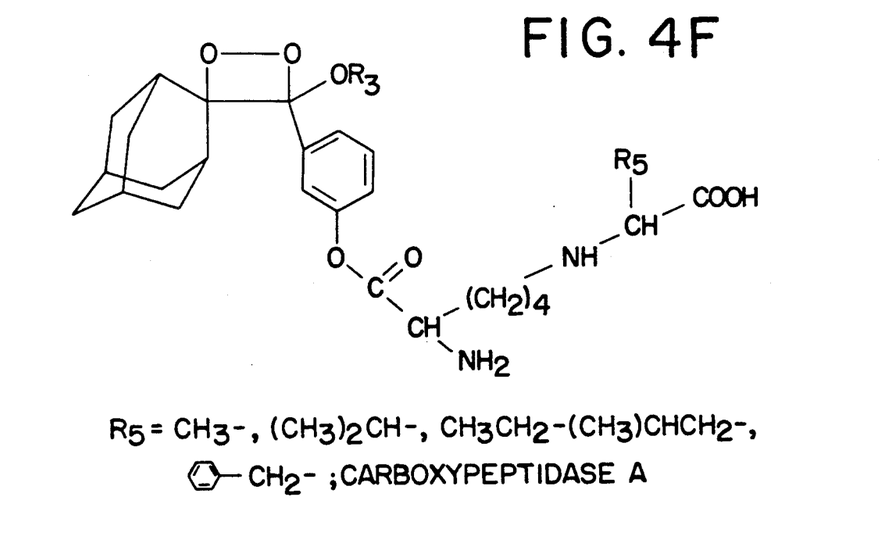
FIG. 4F is a carboxypeptidase/trypsin double-trigger substrate.
Figure 4G:
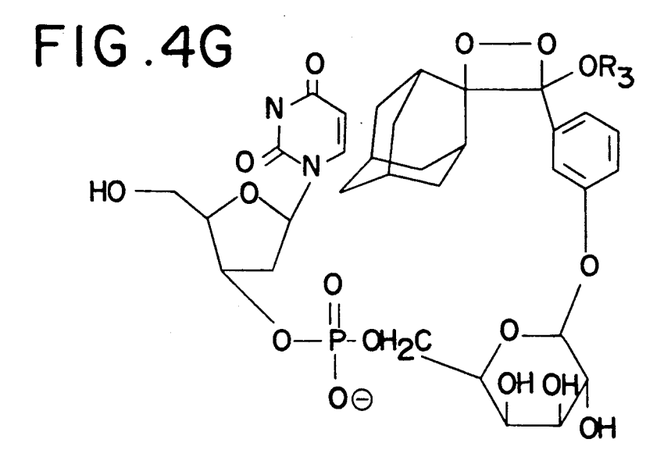
FIG. 4G is a phosphodiesterase/B-galactosidase double-trigger substrate.
Figure 4H:
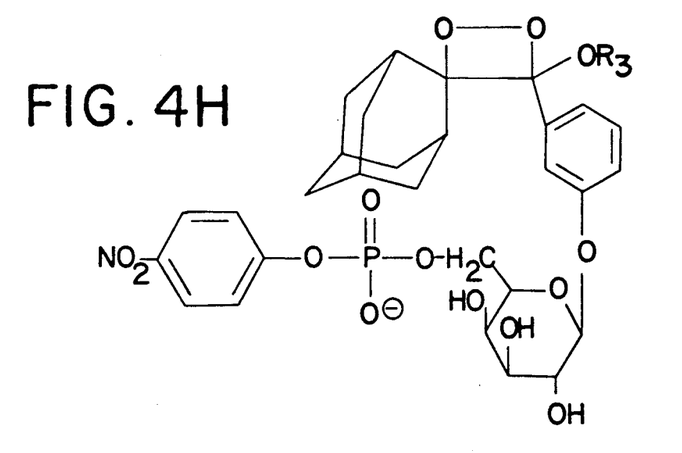
FIG. 4H is a nuclease/B-galactosidase double-trigger substrate.

FIG. 3 shows a variation of the process illustrated in FIG. 1 that employs a combination of an enzyme trigger and a chemical trigger rather than two enzymes. In FIG. 3 the dioxetane is 4-[3-(4-phenylalanylsuccinyl)-phenyl]-4-methoxyspiro [1,2-dioxetane-3,2'-adamantane], the first trigger is carboxypeptidase A and the second trigger is hydroxylamine. (It is conceivable that the distance between the two carboxyl functions, 2 carbons in the succinyl derivative, should be increased to 3 or more carbons for increased stability after the first triggering event).

In FIG. 4, several potential structures that could be triggered by two separate events are shown ($R_3$ may be as defined above and is preferably methoxy). The triggering enzymes or compounds are listed below:

| Structure | 1st Trigger | 2nd Trigger |
| --- | --- | --- |
| A | esterase | β-galactosidase |
| B | esterase | phosphatase |
| C | carboxypeptidase | hydroxylamine |
| D | 5'-nucleotidase | phosphatase |
| E | horseradish peroxidase | phosphatase |
| F | carboxypeptidase | trypsin |
| G | phosphodiesterase | β-galactosidase |
| H | nuclease | β-galactosidase |

As indicated above, these double triggered dioxetanes may be used in known immunoassay and nucleic acid hybridization assay formats. They are particularly useful where the target is present in the sample at very low concentrations. For instance in enzyme immunoassays (EIAs) used to detect the presence and/or quantity of target antigen or antibody in a biological specimen, the label (first enzyme in terms of the invention process) is bound to an immune complex that includes the target. The immune complex is formed through antigen-antibody binding. The literature is replete with the procedures used in EIAs to produce such complexes. Once the complex is formed, the invention dioxetane is added to the aqueous media containing the complex, permitting the enzyme carried by the complex to cleave the first protecting group from the dioxetane. Excess second enzyme is then added to the media resulting in the cleavage of the second protecting group from the dioxetane and activating the decomposition of the dioxetane and concomitant light production. The light produced is read with a luminometer or like reading device and recorded. The quantity of light produced may be correlated with the concentration of target in the sample through comparison with like measurements made on samples containing known amounts of target.

In nucleic acid hybridizations the target is single-stranded nucleic acid (either DNA or RNA). If desired the target nucleic acid may be amplified before carrying out the hybridization assay using a polymerase chain reaction process (PCR). Reagents and equipment for carrying out PCR are available commercially. A large number of hybridization assay formats are described in the literature. All of them involve hybridizing the target nucleic acid with a nucleic acid probe that is substantially complementary to the target. The probe is either labeled directly (i.e., the label is bound directly to the nucleic acid probe) or indirectly (i.e., the label is bound to the probe through one or intermediate molecules, usually through intermediate nucleic acid molecules. A preferred nucleic acid hybridization format is described in copending commonly assigned U.S. patent application Ser. No. 340,031 filed Apr. 18, 1989, the disclosure of which is incorporated herein by reference. That format employs a nucleic acid multimer to amplify the amount of enzyme label that may be bound to the target. Once the enzyme-bearing nucleic acid complex is formed, the invention dioxetane is added to the aqueous media containing the complex permitting cleavage of the first protecting group from the dioxetane. The second protecting group is cleaved from the complex through addition of a second enzyme and the resulting luminescence is read as above.

The 1,2-dioxetanes of this invention may be packaged in combination with deprotecting agents as kits for use in standard immunoassays and hybridization assays that employ an enzyme label. In such instances the dioxetane will be selected so that Z is a protecting group that is removed via the action of the label. The deprotecting agent is one that removes the second protecting group, Y. In addition to the dioxetane and deprotecting agent, which will be contained in separate containers, the kit may also include instructions.

EXAMPLES

The following examples are intended to further illustrate the invention. These examples are not intended to limit the invention in any manner.

The abbreviations used in the examples are as follows: TBMS = t-butyldimethylsilane/yl; DIPEA = diisopropylethylamine; LAH = lithium aluminum hydride; THF = tetrahydrofuran; DMAP = 4-dimethylaminopyridine; DCC = dicyclohexylcarbodiimide; TEA = triethylamine.

1. Synthesis of 4-[3-hydroxyl-2-methylnaphthylene-1 phosphoryl)phenyl]-4-methoxyspiro [1,2-dioxetane-3,2'-adamantane]

The process for making this dioxetane is shown in FIG. 5.

Preparation of methyl 3-hydroxybenzoate (compound 2): m-Hydroxybenzoic acid (10g, 72.5 mmol) is dissolved in 100 ml of methanol. After 24 h of refluxing in the presence of a trace quantity of HCl, the solution is cooled and concentrated by rotary evaporation. The solid is dissolved in 200 ml of ethyl ether and extracted with saturated NaHCO$_3$, then saturated NaCl. The solution is dried by passing it through Na$_2$SO$_4$, then concentrated in vacuo. Recrystallization from benzene/cyclohexane should yield a 50-70% yield of methyl 3-hydroxybenzoate.

Preparation of 4-t-butyldimethylsilyloxy-2-methyl-1-hydroxyl-napthylene (compound 4): Between 20 and 40 mmol of 2-methyl-1,4-dihydroxynapthylene (compound 3) and a 10% molar excess of diisopropylethylamine (DIPEA) are dissolved in 10-50 ml of CH$_2$Cl$_2$ in a round bottom flask set on ice. The solution is stirred while a 10-20% excess of t-butyldimethylsilyl chloride (TBMS-Cl) is added slowly. The reaction is monitored by TLC and should reveal conversion of 2-methyl-1,4-dihydroxynapthylene to two products (1- and 4-TBMS). The reaction solution is extracted with water and/or brine (and possibly back-extracted with CH$_2$Cl$_2$), then dried over Na$_2$SO$_4$. The solid is taken up in a small volume of CH$_2$Cl$_2$. The appropriate fractions are taken and then worked-up as above. Nuclear magnetic resonance (NMR) spectroscopy is used to identify the appropriate species, 4-t-butyldimethylsilyloxy-2-methyl-1-hydroxyl-napthylene. Anticipated yield, 15-35%.

Preparation of 1-[N,N-diisopropylamino-2-cyanoethylphosphinyl)oxy-4-t-butyldimethylsilyloxy-2-methyl-napthylene (compound 6): 10-20 mmoles of 4-t-butyldimethylsilyloxy-2-methyl-1-hydroxyl-napthylene is dissolved in 25-50 ml of CH$_2$Cl$_2$ containing a 10% excess of DIPEA. The solution is stirred in ice under an argon atmosphere. A neet solution of N,N-diisopropylamino-2-cyanoethylchlorophosphine (compound 5) is added dropwise over several minutes and the reaction is monitored by TLC. After completion, the ice is removed and the solution is brought up to about 200 ml with CH$_2$Cl$_2$ or ethylacetate. After extraction with brine and drying over Na$_2$SO$_4$, the solution is concentrated to dryness in vacuo. A silica column purification step could be required if less than 95% conversion from 4-t-butyldimethylsilyloxy-2-methyl-1-hydroxyl-napthylene has taken place. The dried powder or foam would be stored under argon at −20° C.

Preparation of 3-hydroxylphenylmethoxymethyleneadamantane (compound 8): A 500 ml three-neck, round bottom flask is fit with a reflux condenser, 125 ml addition funnel, and a nitrogen inlet line with a two-way valve control. After the addition of 200 ml of dry THF, the solution is stirred and cooled under nitrogen on an ice bath. TiCl$_3$ (156 mmol) is added rapidly followed by lithium aluminum hydride (75 mmol) in portions. The ice bath is removed and the solution is permitted to warm to ambient temperature. Upon the addition of triethylamine (86 mmol), the solution is refluxed for 1 h. At this time, a solution of 15-20 mmol of methyl 3-hydroxybenzoate and approximately a 10-20% excess of 2-adamantanone adamantane in about 50 ml of THF are added dropwise over several hours by means of the addition funnel. Refluxing is continued for another several hours. After completion, the cooled solution is quenched by the slow addition of about 50 ml of methanol, then about 100 ml of water. The black mixture is diluted in ether and repeatedly extracted with water until the aqueous phase is no longer colored. The solution is dried over Na$_2$SO$_4$ and concentrated in vacuo. Silica column chromatography is used to purify the desired product, 3-hydroxylphenylmethoxymethylene-adamantane. Ethyl acetate/hexane or methanol/CH$_2$Cl$_2$ solvent systems could be employed. The product (anticipated 10-30% yield; probably an oil) is characterized by NMR.

Preparation of [(3-(4-hydroxyl-2-methylnapthylene-1-phosphoryl)phenyl)methoxymethylene] adamantane (compound 9): About 10 mmol of Compound 8 (3-hydroxylphenylmethoxy-methyleneadamantane) is dissolved and stirred in 10-50 ml of 0.3 M 1H-tetrazole in CH$_3$CN. A 2-10 fold molar excess of 1-(N,N-diisopropylamino-2-cyanoethylphosphinyl)oxy-4-t-butyl-dimethylsilyloxy-2-methyl-napthylene dissolved in a small portion of CH$_3$CN is added slowly. The progress of the reaction is followed by TLC. After completion of the reaction, the solution is diluted with ethyl acetate and extracted with NaHCO$_3$, then brine. After drying and concentration, the product is treated with small portions of 0.1 M iodine in 1:1:8 (v/v/v) lutidine/H$_2$O/THF until the mixture remains brownish for at least one minute. Upon another round of extraction, drying and concentration, the material is treated with 10 ml of neet t-butylamine for 30 min at room temperature, then dried in vacuo. The solution is diluted in CH$_2$Cl$_2$, extracted and dried as above. A 2-fold molar excess of 1 M tetrabutylammonium fluoride and 2 M HF in pyridine is added and the removal of the silyl protection is monitored by TLC. After work-up as above, [(3-(4-hydroxyl-2-methylnapthylene-1-phosphoryl)phenyl)methoxymethylene] adamantane is isolated by silica column and characterized by NMR.

Preparation of 4-[3-(4-hydroxyl-2-methylnapthylene-1-phosphoryl)phenyl]-4-methoxyspiro [1,2-dioxetane-3,2'-adamantane] (compound 10): Several milligrams of [(3-(4-hydroxyl-2-methylnapthylene-1-phosphoryl)phenyl) methoxymethylene] adamantane are dissolved in 5–10 ml of CH$_2$Cl$_2$ in an appropriate tube for photooxygen. About 20–60 mg of Sensitox 1 (Rose Bengal bound to polystyrene) is added. Oxygen is bubbled through the solution for about 5 minutes, then the tube is placed in a dry/ice/isopropanol bath (−78° C.). The sample is irradiated for 10–90 minutes with a 1000 W sodium lamp (such as the GL LUcalox) filtered for a UV cutoff. TLC is used to determine the extent of the reaction. Upon completion, the Sensitox is removed by filtration and the product is concentrated in vacuo. 4-[3-(4-hydroxyl-2-methylnapthylene-1-phosphoryl)phenyl]-4-methoxyspiro [1,2-dioxetane-3,2'-adamantane] is purified by recrystallization from a suitable solvent such as pentane or hexane.

2. Synthesis of 4-[3-(4-phenylalanylsuccinyl) phenyl]-4-methoxyspiro [1,2-dioxetane-3,2,-adamantane]

The process for making this dioxetane is shown in FIG. 6.

Preparation of N-succinylphenylalanine methyl ester (compound 12): About 100 mmoles each of succinic anhydride 4-[3-(4-hydroxyl-2-methylnapthylene-1-phosphoryl)phenyl]-4-methoxyspiro [1,2-dioxetane-3,2'-adamantane], phenylalanine methyl ester (compound 11), and DMAP are added together in about 100 ml of pyridine in a 250 ml round bottom flask stirred at room temperature under an argon atmosphere. After about 2 h, TLC reveals conversion to compound 12. The product is isolated by silica column chromatography and concentrated to dryness. Anticipated yield 50–70%.

Preparation of [(3-(4-phenylalanyl methyl ester succinyl)phenyl) methoxymethylene] adamantane (compound 13): About 10 mmol of 3-hydroxylphenylmethoxymethyleneadamantane and a 10-50% excess of N-succinylphenylalanine methyl ester are dissolved and stirred in 10–50 ml of dioxane. After 10–20 mmol of DCC are added, the solution is stirred for 18 h at room temperature. TLC reveals the formation of compound 13. The solution is diluted to about 100 ml with ethyl acetate, filtered and extracted with brine. The solution is dried over Na$_2$SO$_4$, evaporated to a small volume in vacuo and loaded onto a silica column. The product is purified by step-gradient elution with an appropriate solvent system (e.g., methanol in CH$_2$Cl$_2$ or pyridine in ethyl acetate). Appropriate fractions are collected and evaporated. Expected yield 10–30%.

Preparation of [(3-(4-phenylalanylsuccinyl)phenyl) methoxymethYlene] adamantane (compound 14): 1–5 mmoles of (3-(4-phenylalanyl methyl ester succinyl)-phenyl) methoxymethylene] adamantane are dissolved in acetonitrile (about 50 ml). About 2 ml of TEA are added and the formation of [(3-(4-phenylalanylsuccinyl)phenyl) methoxymethylene] adamantane is monitored by TLC. It could be necessary to add a few small aliquots of H$_2$O to increase the rate of hydrolysis. Complete conversion to [(3-(4-phenylalanylsuccinyl)phenyl) methoxymethylene] adamantane is anticipated. The solution is then evaporated to dryness. If H$_2$O was added the material is then co-evaporated twice from pyridine and twice from toluene. The product is precipitated as the TEA salt from an appropriate solvent such as hexane or dioxane.

Preparation of 4-[3-(4-phenylalanylsuccinyl)phenyl]-4-methoxyspiro1,2-dioxetane-3,2'-adamantane] (compound 15): Several milligrams of [(3-(4-phenylalanylsuccinyl)phenyl) methoxymethylene] adamantaneare dissolved in CH$_2$Cl$_2$ (or another somewhat more polar solvent) and photooxidized with Sensitox as described for the synthesis of 4-[3-(4-hydroxyl-2-methylnapthylene-1-phosphoryl)phenyl]-4-methoxyspiro [1,2-dioxetane-3,2'-adamantane] in Example 1 above.

3. Nucleic Acid Hybridization Assay Using the Dioxetane of Example 1

The sandwich hybridization assay described in copending commonly owned U.S. patent application Ser. No. 340,031, filed Apr. 18, 1989 is used. Briefly the hybridization portion of this format is as follows. The sample containing the target single stranded nucleic acid is incubated under hybridizing conditions with a set of capture probes and a set of amplification probes. The capture probes have a segment that is complementary to a portion of the target and a portion that is complementary to an oligonucleotide bound to a solid phase. The amplification probes have a segment that is complementary to the target and a segment that is complementary to an oligonucleotide unit of a nucleic acid multimer composed of a units that are complementary to the mentioned segment of the amplification probes and to an oligonucleotide probe labeled with HRP. After the hybridization of the target to the capture and amplification probes is complete, the complex is incubated with the solid phase bound oligonucleotide under hybridization conditions. After this incubation, materials bound to the solid phase are separated from unbound materials with a wash step. The solid phase bound complex is then incubated with the multimer under hybridizing conditions, again followed by a wash cycle to separate bound from unbound material. The bound material is then incubated with the labeled oligonucleotide probe and the resulting bound material is washed to remove unbound probe.

This format is used together with the dioxetane of Example 1 to detect *Chlamydia trachomatis* DNA as follows. Sets of amplification probes, capture probes, solid phase bound oligonucleotide, multimer and HRP-labeled oligonucleotide are prepared as described in Examples 2 and 7 of said copending application. Sample preparation and hybridizations are carried out as in Example 7.

The first triggering event is initiated by the addition of a small aliquot (20–100 μl) of buffer (pH = 7 to 9, HEPES, MOPS, sodium borate, etc., 0.01 to 0.50 M) containing H₂O₂ (0.1 to 10 mM) and the dioxetane (0.1 to 10 mM) to the tube or microtiter well. After an appropriate time (30-60 min) the reaction can be stopped by the addition of catalase.

Addition of AP in the same buffer causes the second triggering. Enhancing agents such as fluorescein, BSA, detergents (e.g., CTAB) can also be employed. The quantity of AP added is optimized to yield a chemiluminescent reaction in a short time frame (several seconds to minutes). The light output is recorded either on an integrating luminometer or on instant black and white or X-ray film. The amount of light recorded is directly proportional to the amount of *Chlamydia trachomatis* DNA in the original sample.

For the dioxetane of Example 2, the hybridization and labeling of *Chlamydia trachomatis* DNA is performed as described in Example 7 of the copending application except that carboxypeptidase A labeled probe is employed. This probe is prepared in a manner analogous to the HRP and AP probes described in Example 2 of the copending application.

The initial triggering is conducted by adding (20-100 μl) the dioxetane (0.1 to 10 mM) in a buffer (Tris, HEPES, MOPS, etc., pH = 7 to 8) to the tube or microtiter well. After 30-60 min, an aliquot of hydroxylamine (final concentration 0.01 to 0.10 M) is added and the light output is recorded as above.

Modifications of the above described modes for carrying out the invention that are obvious to those of skill in the fields of chemistry, bioassays and related fields are intended to be within the scope of the following claims.

We claim:

1. A stable 1,2-dioxetane of the formula:

wherein X' is a phenyl group substituted with 0 to 2 Cl or I atoms.

2. A method for generating light which comprises
(a) providing a stable 1,2-dioxetane of the formula:

wherein is X' is phenyl group substituted with 0 to 2 Cl or I atoms;
(b) removing the 2-methyl-4-hydroxy-naphthyl group with horseradish peroxidase, and
(c) removing the phosphate group with alkaline phosphatase.

* * * * *